(12) United States Patent
Pipe et al.

(10) Patent No.: US 6,921,195 B2
(45) Date of Patent: Jul. 26, 2005

(54) METHOD AND APPARATUS FOR CHARACTERIZATION OF DEVICES AND CIRCUITS

(75) Inventors: Kevin P. Pipe, Coldwater, MI (US); Rajeev J. Ram, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 10/365,101

(22) Filed: Feb. 12, 2003

(65) Prior Publication Data

US 2003/0152132 A1 Aug. 14, 2003

Related U.S. Application Data

(60) Provisional application No. 60/356,492, filed on Feb. 12, 2002.

(51) Int. Cl.[7] .......................... G01N 25/00; G01K 17/20
(52) U.S. Cl. ............................ 374/43; 374/32; 374/45
(58) Field of Search .......................... 374/112, 10, 30, 374/32, 45, 43

(56) References Cited

U.S. PATENT DOCUMENTS

| | | | | |
|---|---|---|---|---|
| 4,555,764 A | * | 11/1985 | Kuehn | 374/29 |
| 5,678,924 A | | 10/1997 | Naquin et al. | |
| 5,743,641 A | | 4/1998 | Geiger | |
| 5,940,784 A | * | 8/1999 | El-Husayni | 374/43 |
| 5,994,154 A | * | 11/1999 | Morikawa | 257/85 |
| 5,997,174 A | * | 12/1999 | Wyland | 374/43 |
| 6,101,200 A | | 8/2000 | Burbridge et al. | |
| 6,203,191 B1 | * | 3/2001 | Mongan | 374/43 |
| 6,367,970 B1 | * | 4/2002 | Danielson | 374/43 |
| 6,491,426 B1 | * | 12/2002 | Schonath et al. | 374/45 |
| 6,748,129 B2 | * | 6/2004 | Braun et al. | 374/32 |
| 2003/0012252 A1 | * | 1/2003 | Bender | 374/32 |

FOREIGN PATENT DOCUMENTS

| | | | |
|---|---|---|---|
| DE | 19829716 A1 | 1/2000 | |
| EP | 1085624 A1 | 3/2001 | |
| GB | 2218566 | 11/1989 | |
| JP | 60046431 A | * 3/1985 | ............ G01J/1/02 |
| JP | 63028083 | 2/1999 | |

OTHER PUBLICATIONS

Pipe et al.: "Comprehensive Heat Exchange Model for a Semiconductor Laser Diode," IEEE Photonics Technology Letters; vol. 15, No. 4, Apr. 2003; XP-002279368; pp. 504-506.
PCT Search Report: PCT/US03/04089 dated May 26, 2004.

* cited by examiner

*Primary Examiner*—Diego Gutierrez
*Assistant Examiner*—Mirellys Jagan
(74) *Attorney, Agent, or Firm*—Daly, Crowley, Mofford & Durkee, LLP

(57) ABSTRACT

A method and apparatus for performing characterization of devices is presented. The characteristic of the device are determined by obtaining a first temperature measurement in a first location of a device, obtaining a second temperature measurement, computing the difference between the temperature measurements and, using the temperatures and/or the temperature difference, a characteristic of the device is determined.

8 Claims, 6 Drawing Sheets

METHOD AND APPARATUS FOR CHARACTERIZATION OF DEVICES AND CIRCUITS

CROSS REFERENCE TO RELATED APPLICATIONS

This application claims priority under 35 U.S.C. § 119(e) to provisional patent application Ser. No. 60/356,492 filed Feb. 12, 2002; the disclosure of which is incorporated by reference herein.

STATEMENT REGARDING FEDERALLY SPONSORED RESEARCH

This invention was made with government support under Grant Number BX-7556 awarded by the U.S. Air Force. The government has certain rights in the invention.

BACKGROUND OF THE INVENTION

The reliable functioning of optical components is of critical importance in optical systems, which typically have small tolerances. Parameters such as device efficiency (which describes the amount of conversion between electrical and optical energy) govern the performance of an optical system. For example, optical systems which utilize semiconductor lasers as light sources can lose performance due to heating of the laser at high power levels and the consequent well-known phenomenon of efficiency rollover.

Prior art methods for the characterization of optical devices have relied upon measurements made by calibrated optical detectors, which produce a signal proportional to the incident light power. See, for example, U.S. Pat. Nos. 5,678,924 and 5,743,641. These methods can be hampered in situations where such detectors are not available (as is true for certain wavelengths of light) or are not able to be positioned in the path of the light. The latter can be the case in integrated photonic systems in which optical elements emit light laterally into immediately adjacent fabricated components. Additional complications with calibration arise when optical systems employ devices at many different wavelengths.

The use of a thermal sensor in the control of laser power has been previously proposed in U.S. Pat. No. 6,101,200. However, this prior method relies upon an optical detector to determine the desired amount of optical power; device temperature is then probed at this bias point and a thermal sensor is later used in conjunction with a thermoelectric cooler merely for feedback control. Since this prior method relies on an optical detector, this prior method is inapplicable in the case of integrated photonic systems, and also is not appropriate for the determination of device parameters over a range of bias.

In view of the foregoing it would be desirable to provide a method and apparatus for characterizing devices and circuits. It would be further desirable to provide such a method and apparatus using a thermal sensor to measure optical device and circuit parameters.

SUMMARY OF THE INVENTION

A method and apparatus for performing characterization of devices is presented. The characteristic of the device is determined by obtaining a first temperature measurement in a first location of a device, obtaining a second temperature measurement, computing the difference between the temperature measurements and, using the temperatures and/or the temperature difference, determining a characteristic of the device.

BRIEF DESCRIPTION OF THE DRAWINGS

The invention will be better understood by reference to the following more detailed description and accompanying drawings in which.

DETAILED DESCRIPTION

A method and apparatus for characterization of photonic devices and circuits is presented. A thermal sensor is used to measure an internal or a surface temperature of a device. The sensor is then moved (or a second sensor is used) to measure a temperature in a second location. Alternately a reference temperature may be used. The difference between the two temperatures is determined. The temperatures and/or the temperature difference are related mathematically to characteristics (for example, the power being dissipated) of the device. Device characteristics are then derived by mathematical means. The device characteristics may include, but are not limited to, optical power, power dissipation, radiated power, spontaneous emission power, electron temperature, optical absorption, optical gain, heat transfer coefficient, threshold current, spontaneous emission efficiency, stimulated emission efficiency and thermal impedance.

The invention described herein uses a thermal sensor to measure optical device parameters at any particular bias point; since the sensor does not rely on light being incident on the sensor, the sensor does not require thee use of an optical detector, and is applicable to integrated photonic systems.

Figure 1:
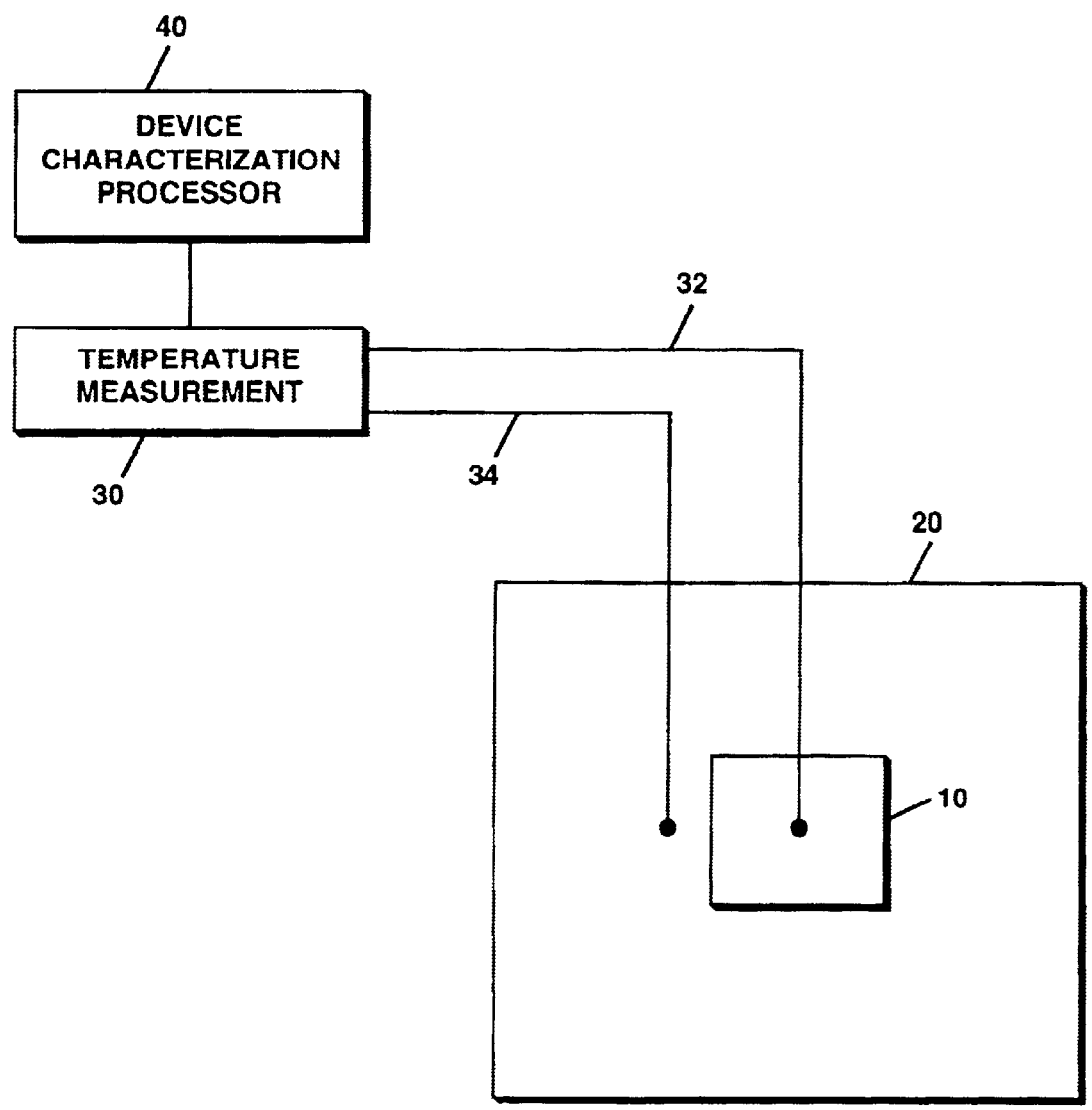
FIG. 1 is a diagram of an apparatus for measuring a single device.

Referring now to FIG. 1, a temperature measurement configuration is shown. A device 10 is mounted on a substrate 20. A first thermal probe 32 is brought to the device 10 for measuring a temperature on or near the device. A second thermal probe 34 is brought to the substrate 20 proximate the device 10. Both thermal probes are connected to temperature measurement device 30. The thermal probes measure the temperature and provide an indication of the measured temperature to the temperature measurement device. The temperature measurement device receives the signals from each thermal probe and from the received signals determines the temperatures measured at the distal end of the thermal probes. The output of temperature measurement device 30 is coupled to a device characterization processor 40. The device characterization 40 receives data from temperature measurement device 30 and uses this data to determine a characteristic of device 10. The data may be the temperatures measured by the thermal probes or may be the difference between the temperatures measured by the thermal probes.

Figure 2:
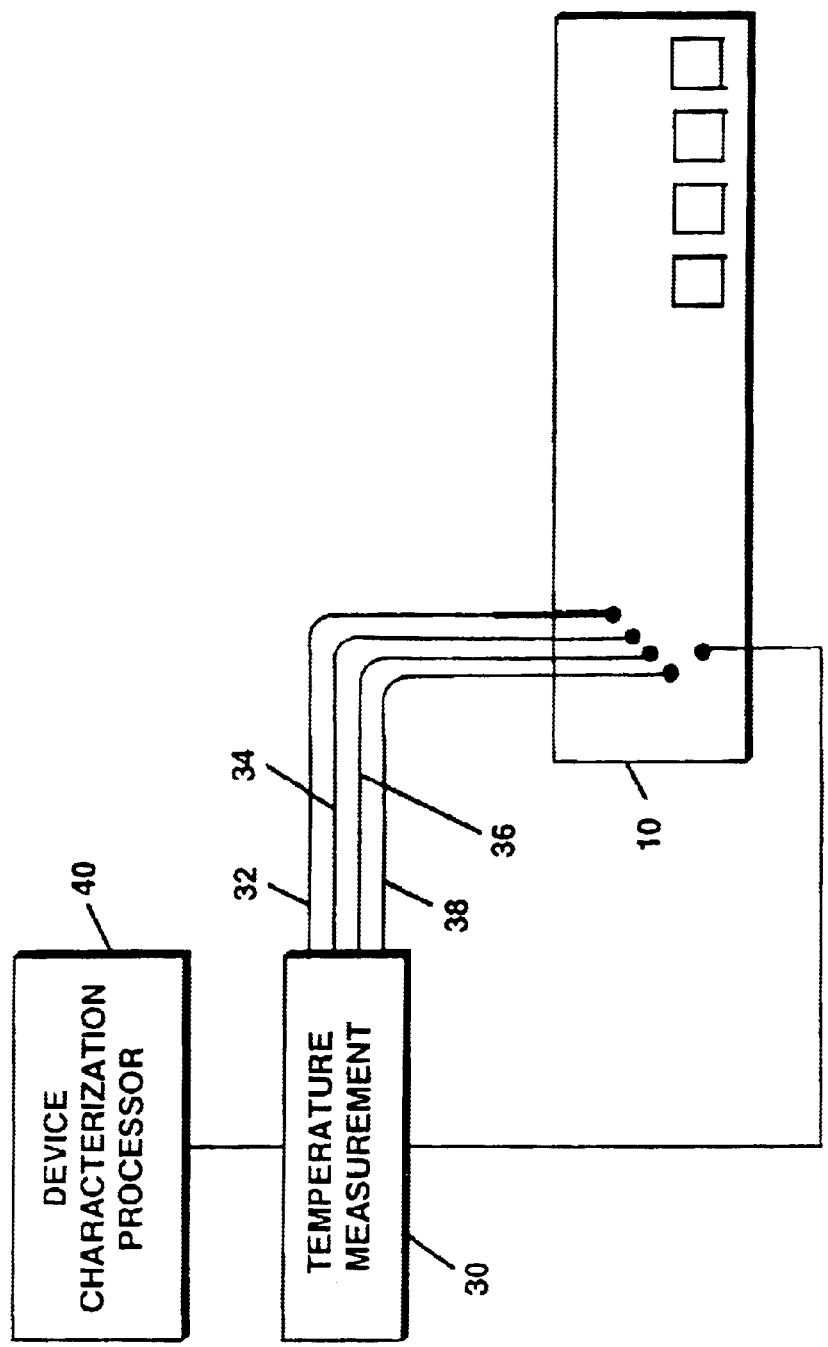
FIG. 2 is a diagram of an apparatus for measuring multiple devices.

Referring now to FIG. 2, another temperature measurement configuration is shown. In this configuration there are a total of four thermal probes 32, 34, 36, 38 coupled to device 10 and to temperature measurement device 30. The four probes are positioned at different locations on device 10. The output of temperature measurement device 30 is coupled to a device characterization processor 40. The device characterization 40 receives data from temperature measurement device 30 and uses this data to determine a characteristic of device 10.

The present invention can be utilized to determine one or more characteristics of several different types of devices. For example the device may be a laser diode, a waveguide amplifier, a waveguide modulator and a detector. In the case where the device comprises a laser diode fabricated on the surface of a thick substrate, temperature sensors are placed on the substrate and on the top of the device. The temperature difference in this case is accurately approximated by a simple thermal impedance model and is proportional to the power dissipated in the laser. Above laser threshold, the power supplied to the device has a term that varies as the square of the current, while the (stimulated optical) power which leaves the device and is not thermally dissipated is proportional to the current. By taking temperature data over a range of current, mathematically taking the derivative, and matching slope/intercept, both the geometric thermal impedance factor and the stimulated optical power efficiency are calculated. The spontaneous emission power is calculated in a similar manner. One advantage of the presently disclosed invention is that the geometric factor can be determined experimentally without recourse to analytic approximation.

In the case of a circuit comprising a collection of laterally interconnected devices operating at different wavelengths on the same surface, the present invention can be used to determine the optical parameters of any device under working conditions while the other devices are simultaneously operating, without recourse to invasive probing or any kind of calibration. By using this method to calculate the true emitted power from a laser, the collection efficiency of an optical detector may be calibrated.

Thermal management is a critical issue in the performance of semiconductor laser diodes and other optoelectronic devices. Characteristic parameters such as device efficiency, stability, and lifetime are strongly dependent on operating temperature. While internal heating and cooling sources such as recombination, Joule heating, and thermoelectricity have been studied extensively, external heat exchange models that describe the transport of energy to and from a device have focused primarily on the mechanism of thermal conduction. Analysis of convective effects has been very limited.

A comprehensive model for external energy exchange that examines other pathways such as convection and radiation are presented. By taking into account all such mechanisms, new design strategies for temperature control (for example, enhancement of convective heat flow in broad-area devices) are achieved. Additionally, at a method for the wafer-scale testing of the light power of photonic integrated circuits that relies only on non-invasive thermal measurement is also achieved.

There are three mechanisms by which a device can exchange heat energy with its environment: conduction, convection, and radiation.

Conduction occurs across a temperature gradient through atomic vibrations and collisions in which no translational motion of the individual particles takes place; it is thus typical of solids. The heat equation that governs steady-state thermal conduction in a region with thermal conductivity k is given by $\nabla \cdot k \nabla T = -q$ where q is the power generated per unit volume. For quasi-one-dimensional heat flow in a source-free region, the temperature difference $\Delta T$ between a boundary heat source and a point within the region can be approximated using a thermal impedance model as $\Delta T = Z_T Q_{cond}$ where $Z_T$ is a geometry-dependent impedance and $Q_{cond}$ is the power generated by the source. In this approximation, the temperature dependence of the thermal conductivity is also neglected. For example, heat conduction in one dimension can be described by the thermal impedance $$Z_T^{1D} = \frac{L}{kA}$$

where L and A are (respectively) the thickness and area of the region across which $\Delta T$ is maintained.

Convection occurs across a temperature gradient in which heat energy is transferred by the translational motion of individual particles; it is thus typical of fluids. The heat transferred by convection from a planar source surface of area A and temperature $T_{surf}$ to a surrounding fluid at temperature $T_{amb}$ is given by $Q_{conv} = hA(T_{surf} - T_{amb})$ where the heat transfer coefficient h depends on parameters such as the fluid's velocity and specific heat and the nature of the fluid/surface contact. While conduction and radiation are the primary mechanisms of heat transfer near the surface, where the fluid is stationary, it is common practice to include the total heat transfer from a surface to a moving fluid into the convection model.

Radiation occurs when charged carriers transmit energy in the form of electromagnetic waves; this energy can be acquired by the carriers thermally (as in blackbody radiation) or through electrical pumping (as in optoelectronic devices). For typical device temperatures, the blackbody term is small, but for optical devices such as laser diodes the radiated power due to electrical pumping can be significant.

In the steady state, the power generated by a device is balanced by the power removed from the device, and we can write $$Q_{gen} = Q_{cond} + Q_{conv} + Q_{rad} \quad (1)$$

For a laser diode, the radiated power below and above threshold can be written as $$Q_{rad} = \begin{cases} \eta_{LED} I & (I < I_{th}) \\ \eta_{LED} I_{th} + \eta_d (I - I_{th}) & (I \geq I_{th}) \end{cases} \quad (2)$$

where the differential efficiencies $\eta_{LED}$ and $\eta_d$ are device-dependent and represent the fraction of recombining carriers that contribute to (respectively) spontaneous and stimulated emission.

For a semiconductor laser diode structure composed of a thin active region in contact with a thick substrate that also contacts a heat sink, we consider the typical case in which recombination and absorption are restricted to the vicinity of the active region and Joule heating in the substrate is small. Under these conditions, the bias power IV that is injected at the contacts is almost completely dissipated near the active region. The heat exchange balance for the laser diode can be written, accounting for conduction through the substrate, convection from the top surface, and radiation from the active region, as $$IV = \frac{\Delta T}{Z_T} + A_{eff} h (T_{surf} - T_{amb}) + Q_{rad} \quad (3)$$

where $\Delta T = T_{surf} - T_{hs}$ is measured between the top surface electrical contact and the heat sink. Due to lateral heat spreading, the area $A_{eff}$ over which convection occurs is larger than the top contact area; however, it is assumed small enough that air flow remains laminar and convection is proportional to $T_{surf} - T_{amb}$ (as with the thermal impedance model). In this model free convection (i.e. no forced air motion) is used and the small dependence of h on temperature is ignored. Simple two-dimensional finite-element simulations that maintain constant heatsink and ambient temperatures confirm that total convected power remains proportional to surface temperature at different heat source magnitudes and therefore that $A_{eff}$ does not vary with injected power in this approximation.

At zero bias (I=0), convected and conducted power balance, and Equation 3 can be solved to give $$A_{eff} h = \frac{\Delta T_0}{Z_T (T_{amb} - T_{surf})_0} \quad (4)$$

Below threshold, assuming a low level of spontaneous emission, $$Z_T IV = \Delta T - \Delta T_0 \frac{T_{surf} - T_{amb}}{(T_{surf} - T_{amb})_0} \quad (5)$$

and $Z_T$ can be determined through thermal measurement below threshold.

To quantify heat exchange in actual devices, two semiconductor laser diodes were examined: a ridge-waveguide InP-based device that has a small top contact area and an oxide-stripe GaAs-based device that has a large contact area.

Beginning with the a ridge-waveguide InP-based device, a 15×500 $\mu m^2$ 5-QW InGaAsP/InP laser emitting at $\lambda$=1.55 $\mu m$ that sits atop a 100 $\mu m$-thick InP substrate that is mounted on a large (4×3×0.4 $cm^3$) gold-plated copper block heatsink. The copper block is cooled from below by an external Peltier cooler, and a thermistor located approximately 5 mm from the laser is used for heatsink feedback control. To perform temperature measurements, 25×2 $\mu m^2$ NIST-traceable microthermocouples that have an accuracy of 200 mK and a resolution of 10 mK are used. Surface temperature $T_{surf}$ is measured directly on the top surface contact, and heatsink temperature $T_{hs}$ is measured on the heatsink approximately 50 $\mu m$ from the substrate and just outside the light path. Surface temperature was measured at several locations and averaged; the variation across the surface was less than 200 mK.

Figure 3:
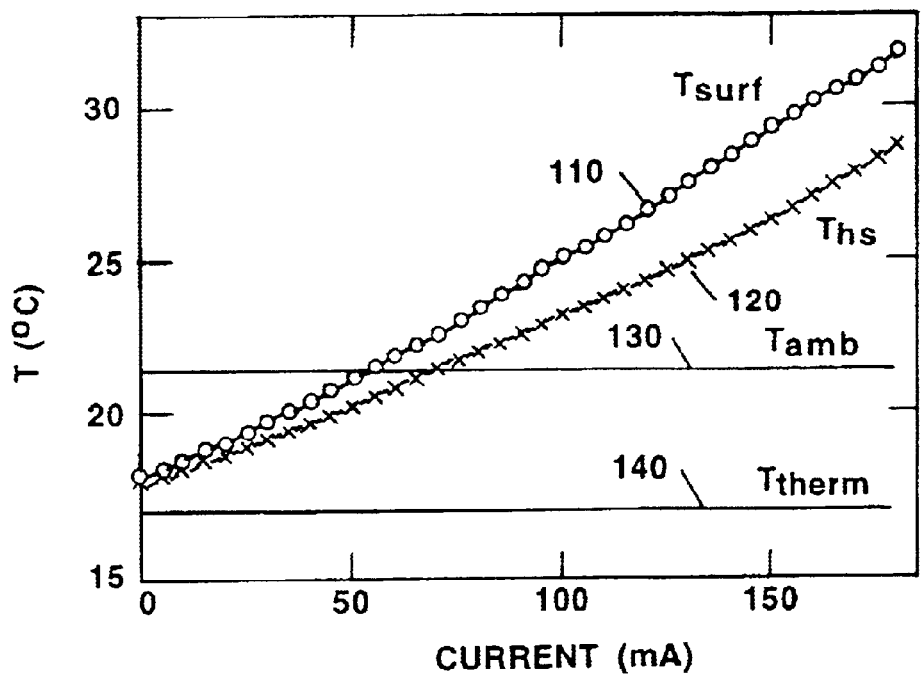
FIG. 3 is a graph of measured temperatures of laser surface, heat sink, ambient air and thermistor set temperature.
Figure 4:
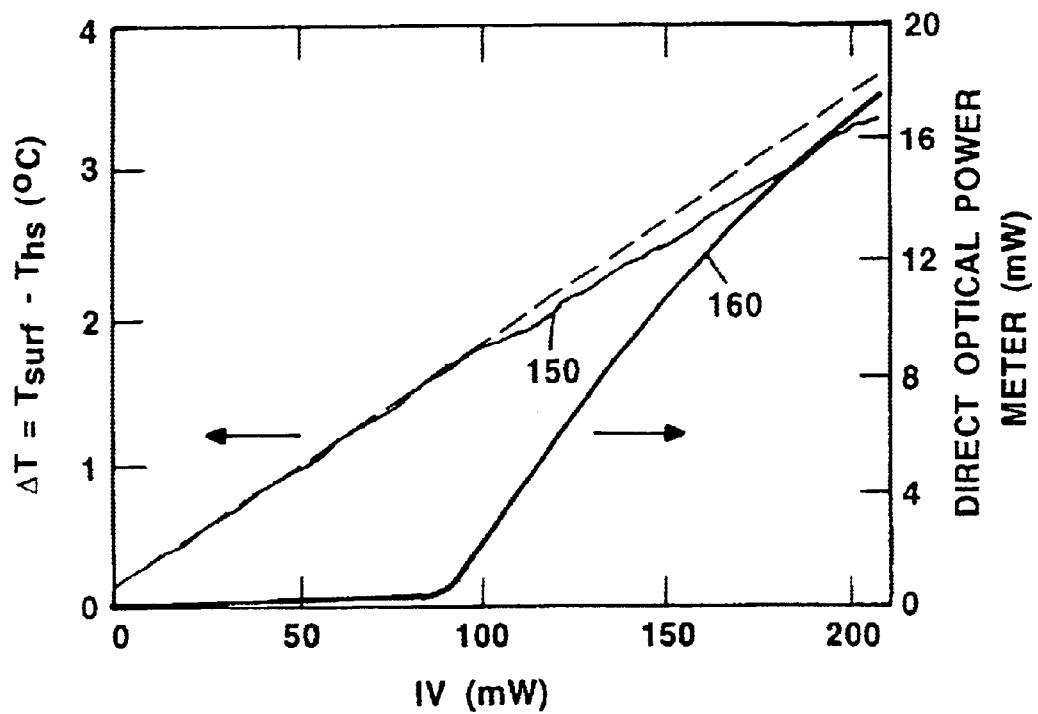
FIG. 4 is a graph showing temperature deviation and optical power versus bias power.

FIG. 3 shows experimental data for this laser structure. The surface temperature 110, heastsink temperature 120, ambient temperature 130 and thermistor temperature 140 are shown. A series resistance of 0.9$\Omega$ in the wires of the IV' power source were measured and taken into account by setting IV=IV'-$I^2 R_{series}$. Although the thermistor is maintained at 17° C., the large-area cooler is unable to effectively control the heat sink temperature near the laser. Referring now to FIG. 4, it can be seen that $\Delta T$ 150 exhibits a kink at threshold due to the sudden increase in radiated power. By plotting the right side of Equation 5 versus IV (line 160) and fitting the slope below threshold, $Z_T$ was determined to be 19.6 K/W. This value is close to previously reported values for geometrically similar InP-based laser diodes that were measured by different methods or predicted theoretically. Small discrepancies may be due to thermal gradients in the heat sink (as shown in FIG. 3) which lead to a non-isothermal boundary condition. Using Equation 4, $A_{eff} h$ was measured to be $1.8 \times 10^{-3}$ W/K. Although $A_{eff}$ is unknown, an estimate that assumes one-dimensional heat flow ($Z_T \approx Z_T^{1D}$, k=68 W/mK) yields $A_{eff} \approx 150 \times 500$ $\mu m^2$ and $h \approx 2.4 \times 10^4$ W/m$^2$K, the latter of which is comparable to reported experimental values for micron-scale semiconductor devices.

Figure 5A:
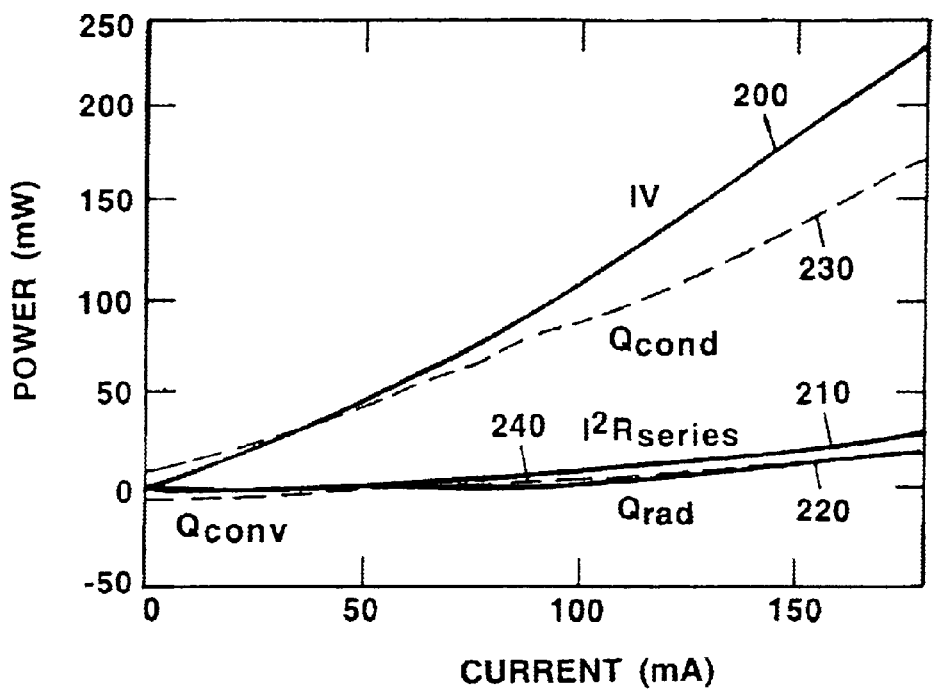
FIG. 5A is a graph of heat exchange terms as derived through thermal probing for a laser at $\lambda=1.55$ $\mu$m.
Figure 5B:
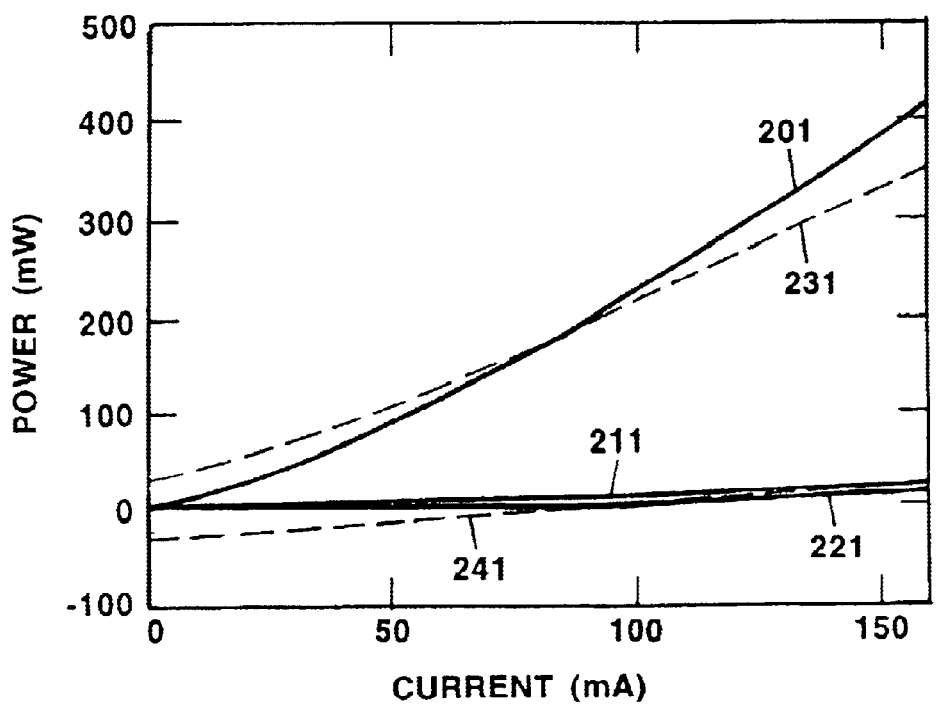
FIG. 5B is a graph of heat exchange terms as derived through thermal probing for a laser at $\lambda=980$ nm.

Having determined quantitatively the parameters for heat exchange, the contributions of the various mechanisms at different bias levels can be plotted, as shown in FIG. 5A for a device operating at $\lambda$=1.55 $\mu m$ and in FIG. 5B for a device operating at $\lambda$=980 nm. The IV 200 and 201, the $I^2 R_{series}$ term 210 and 211, the radiated term 220 and 221, the conduction term 230 and 321, and the convection term 240 and 241 are shown. While conduction 230 and 231 is the dominant term, the convected power 240 and 241 is the same order of magnitude as the radiated power 220 and 221. Also shown are results for a 30×500 $\mu m^2$ oxide-stripe InGaP/InGaAs/GaAs device operating at $\lambda$=980 nm that has a top contact size of 100×500 $\mu m^2$ and a GaAs substrate thickness of 100 $\mu m$. The same setup is used in both cases, and $R_{series}$=0.9 $\Omega$ as before. For the GaAs device, $Z_T$=16.3 K/W and $A_{eff} h$=8.4×10$^{-3}$ W/K were measured. The smaller $Z_T$ and larger $A_{eff} h$ with respect to the InP device are most likely due to heat conduction into the large metal contact; the InP contact is only 15×500 $\mu m^2$ and is connected to a side contact pad. Estimating $Z_T \approx Z_T^{1D}$ as before, it can be found that $A_{eff} \approx 225 \times 500$ $\mu m^2$ and $h \approx 7.5 \times 10^4$ W/m$^2$K for the GaAs (k=55 W/mK) device. The larger effective area is consistent with the larger contact size, and the greater heat transfer coefficient is most likely due to a more even temperature profile across the broad, high thermal conductivity contact, or possibly due to a greater surface roughness in the metal leading to more nucleation sites for droplet condensation.

Figure 6A:
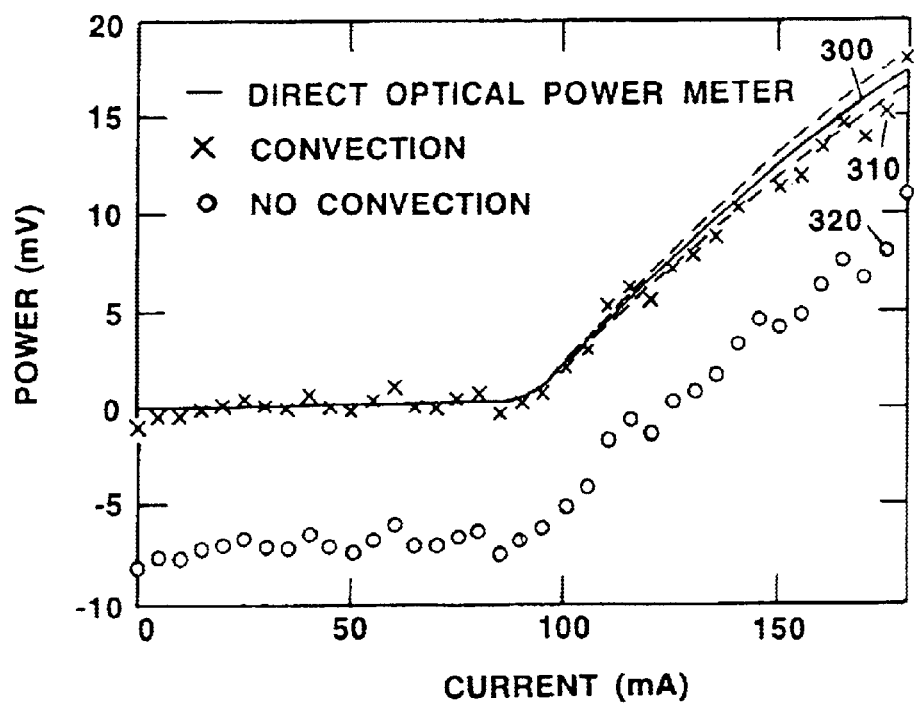
FIG. 6A is a graph of optical power as measured by a detector and derived through thermal probing for a laser at $\lambda=1.55$ $\mu$m.

In order to verify the accuracy of the experimental data, $IV=Q_{cond}-Q_{conv}$ was plotted and compared to measurements taken directly using an optical power meter. As shown in FIG. 6A, the technique of thermal probing can be used to accurately measure the optical power output 300 of the laser diodes. In FIG. 6A the InP laser is modeled both with and without convection (310 and 320 respectively) included in the thermal model. In the zero-convection case, Equation 5 becomes $Z_T IV = \Delta T$; the heat balance of Equation 1 requires that heat conduction must rise accordingly, and $Z_T$ is reduced to 17.1 K/W. Disregarding convection entirely thus results in an error for $Z_T$ of 13%.

Figure 6B:
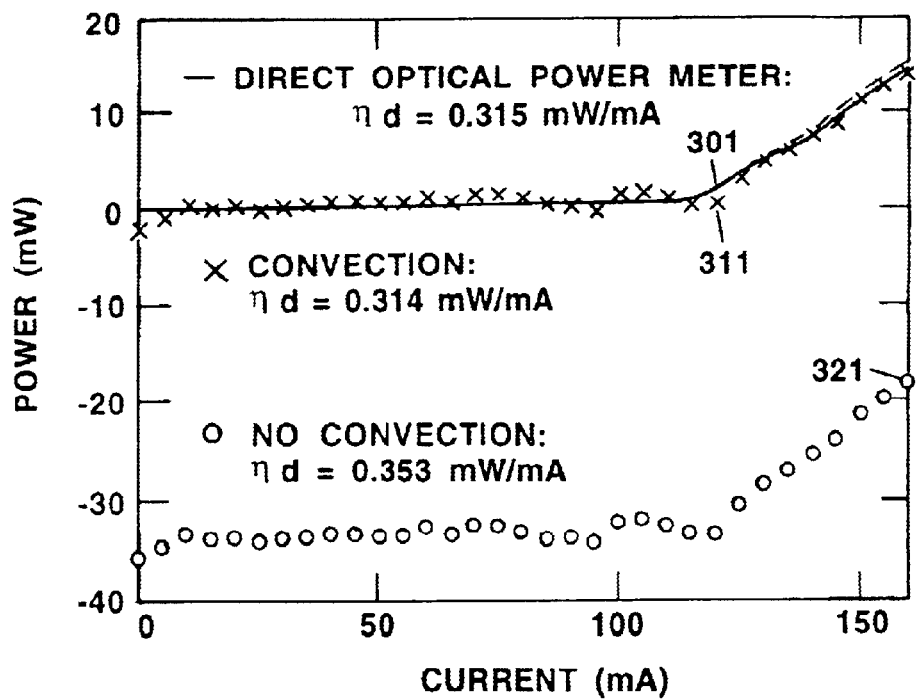
FIG. 6B is a graph of optical power as measured by a detector and derived through thermal probing for a laser at $\lambda=980$ nm.

Since $A_{eff}h$ is small for the InP laser, the zero-bias power convected into the device is likewise small (~6 mW), and $Q_{conv}$ is approximately proportional to IV. For this reason, the convection and zero-convection models differ by only a constant 6 mW (although their values of $Z_T$ are different). In the case of the GaAs laser, however, the zero-bias power convected into the device is larger (~29 mW), and a simple reduction in $Z_T$ does not capture the bias dependence of the convection term. In FIG. 6B the GaAs laser is modeled 301 with the convection term as well as with a zero-convection model (311 and 321 respectively). As before, the elimination of convection from the model reduces $Z_T$ to 14.0 (an error of 14%), but now there is an additional bias-dependent error. This is demonstrated by calculating the laser's differential efficiency above threshold $\eta_d$. By including the bias dependence of the convection term, the error in $\eta_d$ is reduced from 12% to a negligible amount. The differential quantum efficiency $\eta_d(q/h\nu)$ changes from 27.9% to the directly measured value of 24.8%. It is worth noting that the largest error reduction is at high bias values. For the InP laser, the error in $\eta_d$ is 5%. We have not found a reason for the abrupt smoothing of the temperature fluctuations above threshold in the GaAs device.

This technique shows promise as a means for the nondestructive wafer-scale testing of photonic integrated circuits for which detectors are unavailable or are unable to be placed in the light path, such as the case of a laser that is laterally coupled into a waveguide electroabsorption modulator. One advantage of the technique presented here is that a simple setup may be used in a nondestructive way (that does not require calibration) on many different devices during normal operation.

By using microthermocouple probes, experimental quantification of heat flow through the pathways of conduction, convection, and radiation in two optical devices have been determined. Additionally, approximate values of the effective area and the heat transfer coefficient that are used in modeling convection heat exchange have also been determined. Convection is often a non-negligible effect, and its absence in thermal models can result in errors in the measurement of thermal impedance of approximately 14%. The numerical models that are normally employed to predict parameters such as $Z_T$ and $T_0$ for a packaged device can likewise suffer errors from the assumption of an isothermal heatsink boundary condition, which we have shown to fail in certain common geometries.

By carefully accounting for all heat pathways, the use of this technique for the nondestructive wafer-scale testing of optical devices has been disclosed. The location of lasing threshold is determined through temperature measurements, and light output power can be calculated to within a few percent. No prior knowledge of material parameters, geometry, or even light wavelength is necessary. All parameters are obtained experimentally; a careful measurement of the derivative above threshold (where many internal processes have clamped) could yield even better accuracy. This method also shows promise for the determination of other laser parameters such as $\eta_{LED}$ and for application to other devices such as optical amplifiers.

In one embodiment the temperature is measured in the vicinity of an optical device. The temperature is not measured on a surface that is emitting the light signal, possibly in reference to another temperature, while the device is in operation. This temperature or temperature difference is correlated with one or more characteristic parameters of the device by using a mathematical model that relates the temperature or temperature difference to each of the characteristic(s).

Different types of probes can be used. For example thermocouple type probes, photothermal reflectance type probes or the like. Any number of probes may be used. The probes can be placed in a variety of locations, for example, a first probe on one device and a second probe on a substrate, both probes on a substrate, or the probes can be suspended near the device. The present invention is useful for real-time monitoring of devices as well as for testing of devices. The present invention can be used for single devices or for integrated photonic circuits.

In a specific embodiment, a ridge-waveguide laser structure is grown on a thick substrate. The surface temperature at a point on the substrate surface near the laser is related to the power dissipated in the laser by a mathematical expression which takes into account device and substrate material properties and geometries, convection power, and the like.

When the laser is biased above a threshold, a fraction of the electrical power is not dissipated in the device but rather leaves the device as light; this appears as a change in slope on a plot of $\Delta T$ (measured with probes) vs. IV (electrical input power). The location of the slope change gives the laser threshold. The size of slope change gives laser "wall-plug" efficiency (light power out divided by electrical power in).

The thermal impedance $Z_T$ can often be approximated analytically. For example, in the case of a linear heat stripe of width w and length l on a substrate of thickness t and thermal conductivity $\xi$ that is heatsunk at its base, $$Z_T \approx \frac{\ln(4t/w)}{\pi \xi l} \quad \text{Equation (6)}$$

In the case for which thermal conduction dominates heat transfer $$\left(P_{conv} \approx 0, P_{rad} \approx \eta_{stim}\left(\frac{h\nu}{q}\right)(I - I_{th})\right)$$

the power dissipated in the laser $P_{diss}$ can be approximated by:

$$P_{diss} \approx \frac{\Delta T}{Z_T} \approx IV - \eta_{stim}\left(\frac{hv}{q}\right)(I - I_{th}) \qquad \text{Equation (7)}$$

where h is Planck's constant, v is the optical frequency, q is the elementary charge, I is the current, and $I_{th}$ is the threshold current.

Parameters such as $Z_T$ can be determined through the use of this technique. Below threshold, $\eta_{stim}=0$ and $Z_T$ can be calculated through the derivative:

$$Z_T = \frac{d(\Delta T)}{d(IV)} \qquad \text{Equation (8)}$$

The radiated power $P_{rad}$ is then given by:

$$P_{rad} = IV - \frac{\Delta T}{Z_T} \qquad \text{Equation (9)}$$

and the laser efficiency can be determined above threshold by:

$$\eta_{stim} = \left(\frac{q}{hv}\right)\frac{dP_{rad}}{dI} \qquad \text{Equation (10)}$$

or alternatively by measuring the size of the discontinuity in d(ΔT)/dI at threshold:

$$\eta_{stim} = \left(\frac{q}{hvZ_T}\right)\left[\left(\frac{d(\Delta T)}{dI}\right)_{I=Ith^-} - \left(\frac{d(\Delta T)}{dI}\right)_{I=Ith^+}\right] \qquad \text{Equation (11)}$$

The location of threshold can be determined by looking for the kink or change in slope in a plot of ΔT vs. IV. An accurate measure of the derivative can be determined experimentally through lock-in amplifier techniques. By using these mathematical relationships between the measured temperature difference ΔT and the characteristic parameters of the device, the device can be characterized simply and non-invasively through the use of temperature probes.

The above equations can be modified to include other terms such as convective heat exchange and the thermal dependence of parameters such as the thermal conductivity. If the probe measuring $T_{hs}$ is moved for convenience to another location on the substrate away from the heat sink, finite-element modeling can be used to predict the dependence of ΔT on device parameters.

Several device characteristics can be determined from the above-threshold equation $$IV = P_{cond} + P_{conv} + P_{rad}$$
$$= \left(\frac{\Delta T}{Z_T}\right) + \left(Ak(T_{surf} - T_{amb}) + \left(\eta_{spon}\left(\frac{hv}{q}\right)I_{th} + \eta_{stim}\left(\frac{hv}{q}\right)(I - I_{th}) + A\sigma T_{surf}^4\right)\right)$$

where $\Delta T = T_{surf} - T_{hs}$ is measured between the surface of the laser and a nearby point on the heat sink, $Z_T$ is the thermal impedance, $T_{amb}$ is the ambient temperature, A is the device area, k is the convection heat-transfer coefficient, and σ is the Stefan-Boltzmann coefficient. These characteristics include optical power, thermal impedance, heat transfer coefficient, spontaneous emission efficiency, stimulated emission efficiency and threshold current. Similarly, the below-threshold equation $$IV = P_{cond} + P_{conv} + P_{rad}$$
$$= \left(\frac{\Delta T}{Z_T}\right) + \left(Ak(T_{surf} - T_{amb}) + \left(\eta_{spon}\left(\frac{hv}{q}\right)I + A\sigma T_{surf}^4\right)\right)$$

can be used to determine optical power, thermal impedance, heat transfer coefficient, spontaneous emission efficiency, and threshold current.

Figure 7:
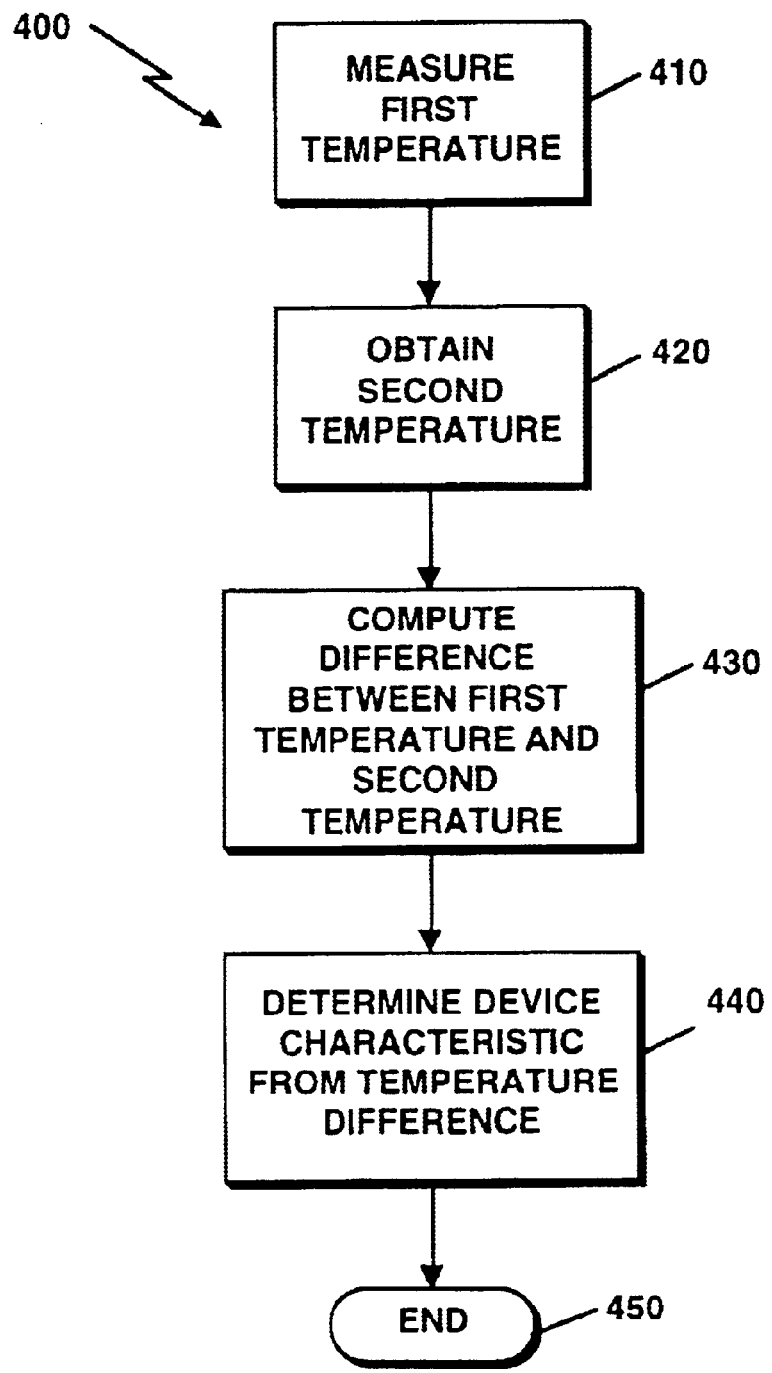
FIG. 7 is a flow chart of the present invention.

A flow chart of the presently disclosed method is depicted in FIG. 7. The rectangular elements are herein denoted "processing blocks" and represent computer software instructions or groups of instructions. The diamond shaped elements, are herein denoted "decision blocks," represent computer software instructions, or groups of instructions which affect the execution of the computer software instructions represented by the processing blocks.

Alternatively, the processing and decision blocks represent steps performed by functionally equivalent circuits such as a digital signal processor circuit or an application specific integrated circuit (ASIC). The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

The first step of the process 400 is shown in step 410 wherein a first temperature is measured. This measurement may be taken in a variety of locations and by any type of probe which measures temperature.

Step 420 is executed next wherein a second temperature measurement is obtained. This measurement may be obtained by a variety of ways. The same probe used to measure the first temperature may be disposed at a different location and the second temperature measurement obtained by this probe. A second probe can be used and the measurement obtained using the second probe. A reference temperature can also be used.

Following step 420, step 430 is executed. At step 430 the difference between the first temperature measurement and the second temperature measurement is computed. This may be computed at the temperature measurement device or by a device characterization processor.

As shown in step 440, a device characteristic is determined from the temperatures and/or the temperature difference. As described above, any one of a number of device characteristics can be determined. The determination can also be made for a number of different devices.

After step 440 is executed, the process 400 ends as shown at step 450.

A method and apparatus for performing characterization of devices has been described. The characteristic of the device are determined by obtaining a first temperature measurement in a first location of a device, obtaining a second temperature measurement, computing the difference between the temperature measurements and, using the temperatures and/or the temperature difference, determining a characteristic of the device.

Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD-ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

What is claimed is:

1. A method for determining a characteristic of a device, the method comprising:

obtaining a first temperature measurement ($T_{surf}$) in a first location of the device;

obtaining a second temperature measurement ($T_{hs}$);

computing the difference ($\Delta T$) between said first temperature measurement and said second temperature measurement; and determining a characteristic of said device using at least one of the group including the temperature measurements and the temperature difference by determining one of optical power ($P_{rad}$), thermal impedance ($Z_T$), heat transfer coefficient (k), spontaneous emission efficiency ($\eta_{spon}$), stimulated emission efficiency ($\eta_{stim}$), and threshold current ($I_{th}$) in accordance with the formula:

$$IV = P_{cond} + P_{conv} + P_{rad}$$
$$= \left(\frac{\Delta T}{Z_T}\right) + \left(Ak(T_{surf} - T_{amb}) + \left(\eta_{spon}\left(\frac{hv}{q}\right)I_{th} + \eta_{stim}\left(\frac{hv}{q}\right)(I - I_{th}) + A\sigma T_{surf}^4\right)\right)$$

wherein IV is the bias power; $P_{cond}$ is the thermal conduction power, and $P_{conv}$ is the thermal convection power, $\Delta T = T_{surf} - T_{hs}$ and is measured between the surface of the device and a nearby point on a heat sink, $T_{amb}$ is the ambient temperature, A is the device area, k is the convection heat-transfer coefficient, σ is the Stefan-Boltzmann coefficient, h is Planck's constant, v is the optical frequency, q is the elementary charge, and I is the applied current.

2. A method for determining a characteristic of a device, the method comprising:

obtaining a first temperature measurement ($T_{surf}$) in a first location of the device;

obtaining a second temperature measurement ($T_{hs}$);

computing the difference ($\Delta T$) between said first temperature measurement and said second temperature measurement; and determining a characteristic of said device using at least one of the group including the temperature measurements and the temperature difference by determining one of optical power ($P_{rad}$), thermal impedance ($Z_T$), heat transfer coefficient (k), spontaneous emission efficiency ($\eta_{spon}$) and threshold current in accordance with the formula:

$$IV = P_{cond} + P_{conv} + P_{rad}$$
$$= \left(\frac{\Delta T}{Z_T}\right) + \left(Ak(T_{surf} - T_{amb}) + \left(\eta_{spon}\left(\frac{hv}{q}\right)I + A\sigma T_{surf}^4\right)\right)$$

wherein IV is the bias power, $P_{cond}$ is the thermal conduction power, and $P_{conv}$ is the thermal convection power, $\Delta T = T_{surf} - T_{hs}$ and is measured between the surface of the device and a nearby point on a heat sink, $T_{amb}$ is the ambient temperature, A is the device area, k is the convection heat-transfer coefficient, σ is the Stefan-Boltzmann coefficient, h is Planck's constant, v is the optical frequency, q is the elementary charge, and I is the applied current.

3. A method comprising:

obtaining a first temperature measurement ($T_{surf}$) in a first location of the device;

obtaining a second temperature measurement ($T_{hs}$);

computing the difference ($\Delta T$) between said first temperature measurement and said second temperature measurement; and determining a characteristic of said device using at least one of the group including the temperature measurements and the temperature difference, wherein said characteristic is power dissipation ($P_{diss}$) determined in accordance with the formula:

$$P_{diss} \approx \frac{\Delta T}{Z_T}$$

wherein $Z_T$ is the thermal impedance, and $\Delta T = T_{surf} - T_{hs}$ and is measured between the surface of the device and a nearby point on a heat sink.

4. A method comprising:

obtaining a first temperature measurement ($T_{surf}$) in a first location of the device;

obtaining a second temperature measurement ($T_{hs}$);

computing the difference ($\Delta T$) between said first temperature measurement and said second temperature measurement; and determining a characteristic of said device using at least one of the group including the temperature measurements and the temperature difference, wherein said device comprises a laser and said characteristic is selected from the group comprising stimulated emission efficiency ($\eta_{stim}$), threshold current ($I_{th}$), thermal impedance ($Z_T$), and power dissipation ($P_{diss}$) determined in accordance with the formula:

$$P_{diss} \approx \frac{\Delta T}{Z_T} \approx IV - \eta_{stim}\left(\frac{hv}{q}\right)(I - I_{th})$$

wherein IV is the bias power, $\Delta T = T_{surf} - T_{hs}$ and is measured between the surface of the device and a nearby point on a heat sink, h is Planck's constant, v is the optical frequency, q is the elementary charge, and I is the applied current.

5. A method comprising:

obtaining a first temperature measurement ($T_{surf}$) in a first location of the device;

obtaining a second temperature measurement ($T_{hs}$);

computing the difference ($\Delta T$) between said first temperature measurement and said second temperature measurement; and determining a characteristic of said device using at least one of the group including the temperature measurements and the temperature difference, wherein said characteristic comprises thermal impedance ($Z_T$), and is determined in accordance with the formula:

$$Z_T = \frac{d(\Delta T)}{d(IV)}$$

where $\Delta T = T_{surf} - T_{hs}$ is measured between the surface of the device and a nearby point on a heat sink, and IV is the bias power.

6. A method comprising:

obtaining a first temperature measurement ($T_{surf}$) in a first location of the device;

obtaining a second temperature measurement ($T_{hs}$);

computing the difference ($\Delta T$) between said first temperature measurement and said second temperature measurement; and determining a characteristic of said device using at least one of the group including the temperature measurements and the temperature difference, wherein said device comprises an optical device and said characteristic comprises radiated power ($P_{rad}$) determined in accordance with the formula:

$$P_{rad} = IV - \frac{\Delta T}{Z_T}$$

wherein IV is the bias power, $\Delta T = T_{surf} - T_{hs}$ and is measured between the surface of the device and a nearby point on a heat sink, and $Z_T$ is the thermal impedance.

7. A method comprising:

obtaining a first temperature measurement ($T_{surf}$) in a first location of the device;

obtaining a second temperature measurement ($T_{hs}$);

computing the difference ($\Delta T$) between said first temperature measurement and said second temperature measurement; and determining a characteristic of said device using at least one of the group including the temperature measurements and the temperature difference, wherein said device comprises a laser and said characteristic comprises laser efficiency above threshold ($\eta_{stim}$) determined in accordance with the formula:

$$\eta_{stim} = \left(\frac{q}{hv}\right)\frac{dP_{rad}}{dI}$$

wherein h is Planck's constant, v is the optical frequency, q is the elementary charge, I is the applied current, and $$P_{rad} = IV - \frac{\Delta T}{Z_T}$$

wherein IV is the bias power, $\Delta T = T_{surf} - T_{hs}$ and is measured between the surface of the device and a nearby point on a heat sink, and $Z_T$ is the thermal impedance.

8. A method comprising:

obtaining a first temperature measurement ($T_{surf}$) in a first location of the device;

obtaining a second temperature measurement ($T_{hs}$);

computing the difference ($\Delta T$) between said first temperature measurement and said second temperature measurement; and determining a characteristic of said device using at least one of the group including the temperature measurements and the temperature difference, wherein said device comprises a laser and said characteristic is laser efficiency above threshold ($\eta_{stim}$) determined in accordance with the formula:

$$\eta_{stim} = \left(\frac{q}{hvZ_T}\right)\left[\left(\frac{d(\Delta T)}{dI}\right)_{I=Ith^-} - \left(\frac{d(\Delta T)}{dI}\right)_{I=Ith^+}\right]$$

wherein h is Planck's constant, v is the optical frequency, $Z_T$ is the thermal impedance, q is the elementary charge, I is the applied current, $\Delta T = T_{surf} - T_{hs}$, and $I_{th}$ is the threshold current.

* * * * *